United States Patent
Chapelet et al.

(10) Patent No.: US 11,905,256 B2
(45) Date of Patent: Feb. 20, 2024

(54) TRIAZINANES AND METHODS OF MAKING THEM

(71) Applicant: FLEXSYS AMERICA L.P., Akron, OH (US)

(72) Inventors: Judicael Jacques Chapelet, Akron, OH (US); Leandro Forciniti, Copley, OH (US)

(73) Assignee: Flexsys America L.P., Akron, OH (US)

( * ) Notice: Subject to any disclaimer, the term of this patent is extended or adjusted under 35 U.S.C. 154(b) by 325 days.

(21) Appl. No.: 17/290,009

(22) PCT Filed: Oct. 22, 2019

(86) PCT No.: PCT/US2019/057357
§ 371 (c)(1),
(2) Date: Apr. 29, 2021

(87) PCT Pub. No.: WO2020/092052
PCT Pub. Date: May 7, 2020

(65) Prior Publication Data
US 2022/0002256 A1    Jan. 6, 2022

Related U.S. Application Data

(60) Provisional application No. 62/753,949, filed on Nov. 1, 2018.

(51) Int. Cl.
  *C07D 251/04*    (2006.01)
  *B60C 1/00*    (2006.01)
  (Continued)

(52) U.S. Cl.
  CPC .......... *C07D 251/04* (2013.01); *B60C 1/0016* (2013.01); *B60C 1/0025* (2013.01);
  (Continued)

(58) Field of Classification Search
  CPC . C07D 251/04; C10L 1/2443; C10L 2230/08; C08L 9/06; B60C 1/0016; B60C 1/0025; B60C 2011/0025; C08K 5/42
  See application file for complete search history.

(56) References Cited

U.S. PATENT DOCUMENTS 4,417,012 A    11/1983    Moniotte
4,532,080 A *  7/1985    Delseth ...................... C08J 5/10
                                                    556/139
(Continued)

FOREIGN PATENT DOCUMENTS

CN    103534236 A    1/2014
CN    107501197 A    12/2017

OTHER PUBLICATIONS

PCT International Search Report for International Application No. PCT/US2019/057357 dated Jan. 20, 2020.

*Primary Examiner* — James C Goloboy
(74) *Attorney, Agent, or Firm* — Sterne, Kessler, Goldstein & Fox P.L.L.C.

(57) ABSTRACT

The present invention is directed to compounds represented by the formula: Formula (i) wherein $R_1$ comprises a hydrogen atom or an alkyl group having 1 to 2 carbon atoms; wherein $R_2$ comprises an alkylene group, an arylene group, or a heterocyclic group; and wherein M comprises a monovalent metallic cation such as sodium, lithium, or potassium; or a multivalent metallic cation such as zinc, nickel, iron, titanium, or cobalt; or an ammonium or alkyl ammonium cation derived by addition of proton (s) to a nitrogenous base.

(Continued)

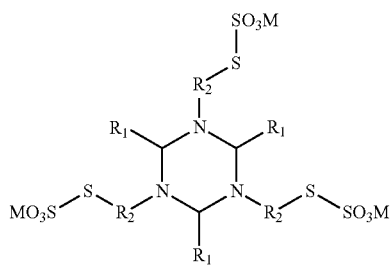

20 Claims, 2 Drawing Sheets

Figure 1:
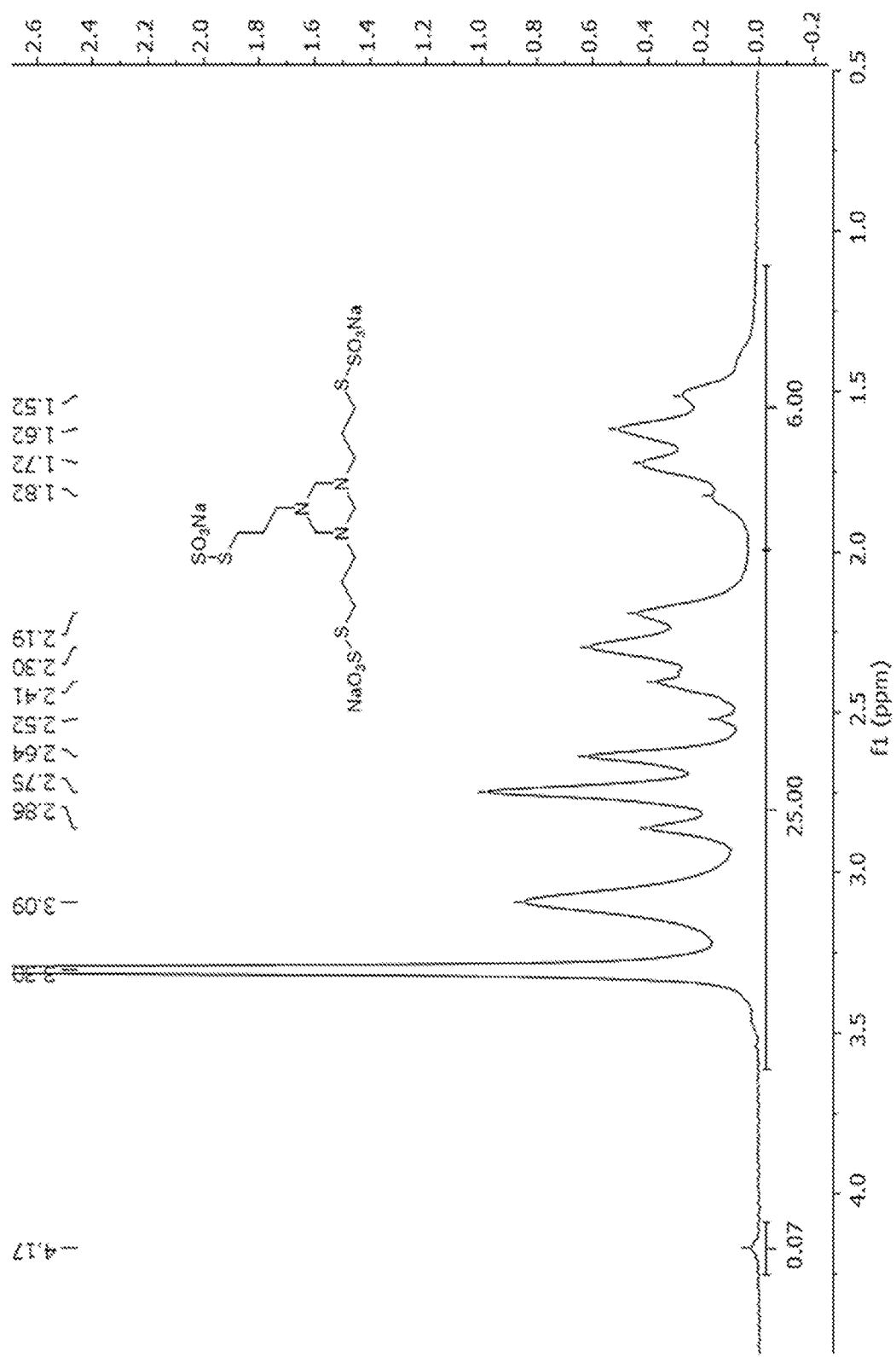

(51) Int. Cl.
*B60C 11/00* (2006.01)
*C08K 5/42* (2006.01)
*C08L 9/06* (2006.01)
*C10L 1/24* (2006.01)

(52) U.S. Cl.
CPC ............ *B60C 11/0008* (2013.01); *C08K 5/42* (2013.01); *C08L 9/06* (2013.01); *C10L 1/2443* (2013.01); *B60C 2011/0025* (2013.01); *C10L 2230/08* (2013.01)

(56) References Cited

U.S. PATENT DOCUMENTS

| | | |
|---|---|---|
| 4,654,271 A | 3/1987 | Mauer et al. |
| 2014/0065337 A1 | 3/2014 | Shiratani et al. |
| 2015/0113858 A1 | 4/2015 | Brewer |

* cited by examiner

TRIAZINANES AND METHODS OF MAKING THEM

FIELD OF THE INVENTION

CROSS-REFERENCE TO RELATED APPLICATION(S)

This application is a national stage filing under 35 USC § 371 of International Application Number PCT/US2019/057357, filed on Oct. 22, 2019, which claims the benefit of the filing date to U.S. Provisional Application No. 62/753,949, filed on Nov. 1, 2018, the entire disclosures of which are incorporated by reference herein.

BACKGROUND OF THE INVENTION

Processes for vulcanizing diene rubbers by heating with sulfur and a vulcanization accelerator have been known for many years. By this process, vulcanized rubber compositions can be obtained that have such desirable properties as high tensile strength, resilience, and fatigue resistance. However, these compositions may lack desirable aging properties. Apart from the addition of antioxidants, which may retard oxidative heat aging, other methods which have been proposed include the use of lower proportions of sulfur and increased proportions of accelerator relative to those which would be employed for a conventional cure, and the partial or complete replacement of sulfur by other cross-linking agents.

However, lowering the ratio of sulfur to accelerator, or replacing the sulfur partially or completely by an amine disulfide, can give vulcanizates having inferior dynamic properties. And the use of bis(sulphenamides) and compounds containing two or more accelerator groupings means that molecular species having accelerator activity as well as those having cross-linking activity are released into the vulcanizing system, so that the freedom for variations in compounding, which is possible when the cross-linking agent and the accelerator are added as separate entities, is lost.

U.S. Pat. No. 4,417,012 discloses vulcanizable rubber compositions that comprise a diene rubber, sulfur, a vulcanization accelerator, and a stabilizer that contains two or more thiosulfate or thiosulfonate groups. The stabilizers disclosed provide vulcanized rubber compositions that demonstrate improved reversion and flex-life.

Articles in which rubber is bonded to metal have also been known for many years, and since the introduction of the steel-belted radial tire, rubber/metal bonding has been extensively studied. Certain substances will act as adhesion promoters, to improve the initial adhesion level between the rubber and the metal, and the maintenance of the adhesion level during accelerated laboratory ageing tests designed to simulate conditions to which the article may be subjected during its service life.

Adhesion promoters used to promote the bonding of brass-coated steel to rubber include cobalt compounds, for example cobalt naphthenate, and resorcinol- and/or melamine-formaldehyde resins used in conjunction with hydrated silica. These adhesion promoters, which can be employed separately or in combination, have disadvantages, and alternative rubber/metal adhesion promoters to those currently employed remain desirable.

U.S. Pat. No. 4,532,080 discloses composites that comprise a sulfur-vulcanizable rubber composition containing a rubber/metal adhesion promoter, and a component having a metal surface in contact with the composition. The adhesion promoters are organic substances containing one or more thiosulfate or thiosulfonate groups. Also disclosed are methods of making articles in which vulcanized rubber is bonded to a metal, which comprise heating a composite to vulcanization temperature to vulcanize the rubber and to bond the rubber to the metal.

Hexamethylene-1,6-bis(thiosulfate) disodium salt, dihydrate available as Duralink HTS from Eastman Chemical Company, Kingsport, Tenn., is used in sulfur-based vulcanization systems to generate hybrid crosslinks. These crosslinks provide increased retention of physical and dynamic properties when exposed to anaerobic conditions at elevated temperatures, such as those that may occur during overcure, when using high curing temperatures, or during product service life. This molecule may be prepared by reacting 1,6-dichlorohexane with sodium thiosulfate in a hot mixture of water-methanol. However, the process and the precursor 1,6-dichlorohexane are relatively expensive. It is therefore desirable to seek and develop new, cost effective molecules bearing multiple organic thiosulfates that provide desirable properties in rubber compositions.

There remains a need in the art for rubber stabilizers that improve one or more of aging, reversion, and adhesion properties.

SUMMARY OF THE INVENTION

In a first aspect, the present invention relates to compounds represented by formula I:

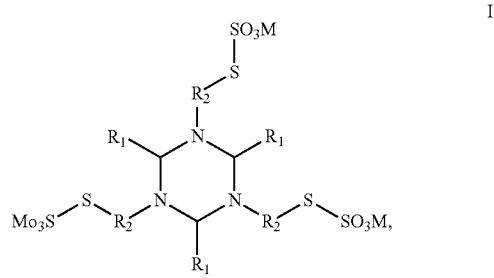

wherein $R_1$ comprises a hydrogen atom or an alkyl group having 1-2 carbon atoms;

wherein $R_2$ comprises an alkylene group, an arylene group, or a heterocyclic group; and wherein M comprises a monovalent metallic cation such as sodium, lithium, or potassium; or a multivalent metallic cation such as zinc, nickel, iron, titanium, or cobalt; or an ammonium or alkyl ammonium cation derived by addition of proton(s) to a nitrogenous base.

In a second aspect, the present invention relates to methods of making the compounds of formula I, that comprise:
reacting a haloalkylamine hydrohalide with a metal thiosulfate to obtain an alkylammonium halide thiosulfate metal salt;
deprotonating the alkylammonium halide thiosulfate metal salt to obtain an alkylamine thiosulfate metal salt; and
reacting the alkylamine thiosulfate metal salt with an aldehyde to obtain the compound of claim 1.

In a further aspect, the present invention is directed to compositions that comprise the compounds of formula I, for example vulcanizable elastomeric formulations, as well as articles made from them.

Further aspects of the invention are as set out below and in the claims that follow. It should be understood that the description and specific examples are intended for purposes of illustration only and are not intended to limit the spirit and scope of the present invention.

DETAILED DESCRIPTION

As utilized herein, the following terms or phrases are defined as follows:

"Adhesion promoter" means a material that increases the adhesion of a polymer composition such as a rubber composition to another material, and especially a metal.

"Antidegradant" refers to a material that inhibits degradation (as caused by for example, through heat, light, oxidation, and/or ozonation), or manifestations thereof, of a composition, formulation or article to which it is added or applied.

"Antifatigue agent" refers to a material that improves the flex fatigue resistance of a composition, formulation or article to which it is added or applied after a period of in-service application time whereby the composition, formulation or article is subjected to thermal, oxidative, ozone and mechanical degradative forces.

"Antioxidant" refers to a material that inhibits oxidative degradation of a composition, formulation or article to which it is added or applied.

"Antiozonant" refers to a material that inhibits ozone exposure degradation of a composition, formulation or article to which it is added or applied.

"Elastomer" means any polymer which after vulcanization (or crosslinking) and at room temperature can be stretched under low stress, for example to at least twice its original length and, upon immediate release of the stress, will return with force to approximately its original length, including without limitation rubber.

"Vulcanizable Elastomeric Formulation" means a composition that includes an elastomer and that is capable of vulcanization when placed under vulcanization conditions.

The compounds of the invention are advantageously believed to increase the density of the cross-linked network of rubber compositions, as evidenced by improved adhesion and reversion properties.

In one aspect, the present invention is directed to compounds represented by formula I:

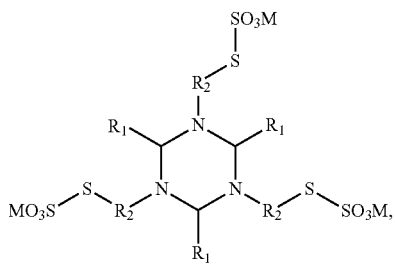

wherein $R_1$ comprises a hydrogen atom or an alkyl group having from 1 to 2 carbon atoms;

wherein $R_2$ comprises an alkylene group having from 1 to 12 carbon atoms, an arylene group having from 5 to 18 carbon atoms, or a heterocyclic group having from 5 to 12 carbon atoms; and wherein M comprises a monovalent metallic cation; a multivalent metallic cation; or an ammonium or alkyl ammonium cation derived by addition of one or more protons to a nitrogenous base.

According to the invention, $R_1$ may thus comprise a hydrogen atom or an alkyl group having 1 to 2 carbon atoms. Alkyl groups useful according to the invention thus include methyl and ethyl.

$R_2$ may comprise an alkylene group, an arylene group, or a heterocyclic group. Alkylene groups useful according to the invention include methylene, ethylene, propylene, and butylene, and more generally may be straight chain or branched alkyl groups having from 1-12 carbon atoms, or from 1-8 carbon atoms, or from 2-5 carbon atoms. Arylene groups useful according to the invention include phenylene, biphenylene, naphthalene, anthracene, indane, and fluorene, and may be substituted or unsubstituted. More generally, arylene groups include any arylene groups having from 5-18 carbon atoms, or from 6 to 12 carbon atoms, or from 6 to 8 carbon atoms, and may be substituted or unsubstituted. Heterocyclic groups that are useful according to the invention include both saturated and unsaturated heterocycles having from 5 to 12 carbon atoms, and aromatic heterocycles, and include indole, benzofuran, benzothiophene, carbazole, benzothiazole, and benzoxazole.

According to the invention, M may comprise monovalent metallic cation such as sodium, lithium, or potassium. Other monovalent metallic cations that are useful include silver, nickel, and thallium.

Alternatively, M may comprise a multivalent metallic cation such as zinc, nickel, iron, titanium, or cobalt. Other multivalent metallic cations useful according to the invention include platinum and palladium.

M may further comprise an ammonium or alkyl ammonium cation derived by addition of one or more protons to a nitrogenous base. These cations may be monovalent or multivalent cations, and include triethylammonium, tetrabutyl-ammonium, benzyltrimethylammonium, dimethyldioctadecylammonium, 2-hydroxyethan-1-ammonium, ethane-1,2-diammonium, benzene-1,4-diammonium, and diphenylethylenediammonium.

Compounds of the invention thus include S,S',S"-((1,3,5-triazinane-1,3,5-triyl)tris(propane-3,1-diyl)) tris(sulfurothioate), S,S',S"-((1,3,5-triazinane-1,3,5-triyl)tris(ethane-2,1-diyl)) tris(sulfurothioate), S,S',S"-((1,3,5-triazinane-1,3,5-triyl)tris(methane-1,1-diyl)) tris(sulfurothioate), S,S',S"-((1,3,5-triazinane-1,3,5-triyl)tris(butane-4,1-diyl)) tris(sulfurothioate), and S,S',S"-((1,3,5-triazinane-1,3,5-triyl)tris(pentane-5,1-diyl)) tris(sulfurothioate).

In another aspect, the invention relates to methods of making the compounds represented by formula I:

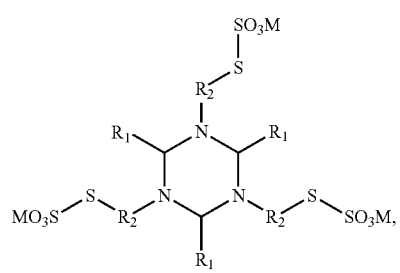

wherein $R_1$ comprises a hydrogen atom or an alkyl group having 1 to 2 carbon atoms;

wherein $R_2$ comprises an alkylene group, an arylene group, or a heterocyclic group, as already described; and wherein M comprises a monovalent metallic cation such as sodium, lithium, or potassium; or a multivalent metallic cation such as zinc, nickel, iron, titanium, or cobalt; or an ammonium or alkyl ammonium cation derived by addition of proton(s) to a nitrogenous base, or as already described.

According to this aspect, the compounds according to the invention may be produced by reacting a haloalkylamine hydrohalide with a metal thiosulfate to obtain a Bunte salt, described herein as an alkylammonium halide thiosulfate metal salt, for example an alkylammonium chloride thiosulfate metal salt. The ammonium halide group of the alkylammonium halide thiosulfate metal salt obtained may be reacted or deprotonated, for example with sodium hydroxide, to obtain the free alkylamine (alkyl ammonium) thiosulfate metal salt. The alkylammonium halide thiosulfate metal salt need not be isolated prior to being deprotonated, and both the alkylammonium halide thiosulfate metal salt and the resulting alkylamine thiosulfate metal salt desirably remain in solution before, during, and after the deprotonation. We have surprisingly discovered that the alkylamine thiosulfate metal salt may then simply be reacted in an aqueous medium with an aldehyde having from 1 to 3 carbon atoms, for example formaldehyde, acetaldehyde, or propionaldehyde, to obtain the desired triazinanes of formula I.

We have thus far demonstrated the invention only with the use of aqueous formaldehyde. However, other suitable formaldehyde sources may be used, such as paraformaldehyde, 1,3,5-trioxane, pure formaldehyde gas, a solution of formaldehyde in solvent, or any combination of the aforementioned. Also, we have been unsuccessful thus far obtaining the desired products of the invention using acetaldehyde and propionaldehyde. However, we believe that acetaldehyde and propionaldehyde may also be used as reactants with routine experimentation, for example with adjustment of the pH of the reaction medium by addition of acid or base, or with use of a solid catalyst support such as alumina and/or silica gel, optionally with microwave heating. See Pareek, et al., Rapid Synthesis and Biological Activities of Some New Benzothiazol-2-ylhexahydro-S-Triazine, Phosphorus, Sulfur, and Silicon, 185:279-286, 2010. It may also be possible to demonstrate the invention using a different solvent system, i.e. N,N-dimethylformamide, dimethyl sulfoxide, an alcohol such as methanol, ethanol, or the like, or any combination of the aforementioned, with or without the use of water.

The haloalkylamine hydrohalides useful according to the invention, may correspond, for example, to the compounds of formula II:

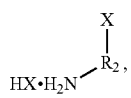

wherein R2 may be an alkylene, arylene, or heterocyclic functionality, as already described with respect to formula I, that links the halide atom to the nitrogen atom, and X is likewise a halogen, for example chlorine, bromine, or iodine. We have found 3-chloropropylamine hydrochloride

to be a suitable haloalkylamine hydrohalide. Other haloalkylamine hydrohalides include, without limitation, 3-bromopropylamine hydrobromide, 2-chloroethylamine hydrochloride, 2-bromoethylamine hydrobromide, 4-chlorobutylamine hydrochloride, 5-chloropentylamine hydrochloride, and the like.

The metal thiosulfates useful according to the invention include those that correspond, for example, with formula III:

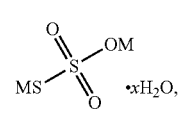

wherein M is a metallic cation as already described with respect to formula I, and x is an integer from 0 to 12. We have found sodium thiosulfate pentahydrate to be a suitable metal thiosulfate. The metal thiosulfate may be anhydrous or may be a hydrate, having for example from one to twelve water molecules associated with it, or even an aqueous solution. Since the reaction may simply be carried out in an aqueous medium, the use of a hydrate or an aqueous solution is entirely satisfactory.

The alkylammonium halide thiosulfate metal salts useful according to the invention include those that correspond, for example, to formula IV:

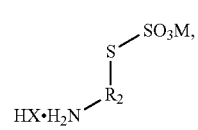

wherein M, $R_2$, and X are as already described just above and with respect to formula I. Similarly, the alkylamine thiosulfate metal salt obtained may correspond, for example, to formula V:

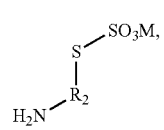

wherein M and $R_2$ are likewise as already described.

As noted, the alkylammonium thiosulfate metal salt obtained may simply be reacted in an aqueous medium with an aldehyde, such as formaldehyde, to obtain the desired triazinanes of formula I. Suitable aldehydes include those that correspond, for example, with formula VI:

VI wherein $R_1$ can be a hydrogen atom or an alkyl group having 1 to 2 carbon atoms, that is, methyl or ethyl, as described above and with respect to formula I.

According to the invention, we thus propose the synthesis and characterization of an organic molecule possessing three sodium thiosulfate moieties linked via a triazinane core. The process may be carried out as a one-pot process with three chemical transformations, using water as the sole solvent of reaction and washing. No tedious extraction techniques are needed, and in certain aspects, the claimed compounds may easily be collected by ordinary vacuum filtration and sparingly washed with water. In certain aspects of the invention, in which formaldehyde is used, isolated yields may be achieved above 95%. In certain embodiments, the only by-product generated through the entire process is aqueous sodium chloride, making the compounds and methods of making them cheap, simple, and environmentally friendly.

In another aspect briefly referenced above, the present invention is directed to a composition that includes at least one compound of the present invention as described above. The specific amount of the compound of the present invention that is included in the composition may vary widely depending on the intended application for the composition. It will be understood by one of ordinary skill in the art that the compositions of the present invention can include one or more compounds of the present invention such that the concentration of each individual compound necessary to achieve the desired efficacy is lower. Further, other known additives may be included in the composition such that a reduced amount of the compound of the present invention may be required to achieve the total desired efficacy.

In one embodiment that is exemplified in detail above, the composition of a present invention is a vulcanizable elastomeric formulation. The vulcanizable elastomeric formulation of the present invention includes at least one elastomer and the compound of the present invention. Preferably, the compound of the present invention is present in the vulcanizable elastomeric formulation in an amount of from 0.1 to 30 parts, preferably from 0.1 to 5.0 parts, per 100 parts elastomer.

The elastomer in the vulcanizable elastomeric formulation may be any vulcanizable unsaturated hydrocarbon elastomer known to one skilled in the art. These elastomers may include, without limitation, natural rubber or any synthetic rubber, for example diene-containing elastomers such as polymers formed from butadiene; isoprene; or combinations of styrene and butadiene, or styrene and isoprene, or styrene, butadiene and isoprene; or polymers formed from ethylene, propylene and diene monomers such as ethylidene norbornadiene or 1,5-hexadiene; or polymers formed from combinations of isobutylene, isoprene, and para-methyl-styrene. The latter potentially could be further halogenated with bromine or chlorine to further extend its usefulness in co-vulcanization with general purpose rubbers such as natural rubber and styrene-butadiene rubber. The vulcanizable elastomeric formulation may optionally also include other additives conventionally used in rubber processing, such as processing/flow aids, extenders, plasticizers, resins, adhesion promoters, antidegradants, coupling agents such as silanes or other promoters of filler-to-polymer interaction, bonding agents, buffers, fillers, pigments, activators, prevulcanization inhibitors, acid retarders, accelerators, fatty acids, zinc oxide, or other compounding ingredients or additives to further enhance the characteristics and/or improve the performance of the vulcanizable elastomeric formulation or the vulcanized elastomeric article from which it is formed Suitable accelerators may include, but not be limited to guanidines, thiazoles, sulfenamides, sulfenimides, dithiocarbamates, xanthates, thiurams, and combinations or mixtures thereof.

The vulcanizable elastomeric formulation of the present invention is useful in the manufacture of vulcanized elastomeric articles such as rubber belts and hoses, windshield wiper blades, vehicle tires and components thereof such as the tread, shoulder, sidewall and innerliner. Accordingly, in another aspect, the present invention is directed to a vulcanized elastomeric article with at least one component formed from the vulcanizable elastomeric formulation of the present invention. In one particular embodiment, the vulcanized elastomeric article is a vehicle tire, and the tire component is a sidewall. Alternatively, the vulcanized elastomeric article may be a reinforcing or structural tire component such as a belt ply compound or construction, a body ply compound or construction, a cover ply, a gum strip, or a composition such as a bead filler, an apex, a wedge, a chafer, a toe guard, a rim guard, or other high modulus component imparting durability to tire service, especially under repeated flexural stresses which may include high service loads.

While the foregoing aspects of the present invention have described utilities primarily focused on compositions related to vulcanized elastomeric article manufacture, it will be understood that the triazinanes of the present invention may also be useful in compositions for other utilities where thiosulfate functionality is desired. Accordingly, and as described above, the present invention in a general aspect is directed to a composition including the compounds of the present invention according to formula I and defined elsewhere herein. In one embodiment, the composition is an adhesion-promoting composition with utility and efficacy for promoting the adhesion of a composition, formulation or article to which it is added or applied, for example where adhesion to fillers such as silica, carbon black, and the like, are desired. Also, adhesion of metal-to-rubber, including zinc, brass, and bronze-coated steel components. The compositions of the present invention therefore include the compounds of the present invention and optionally a carrier for the compound. Suitable carriers are substantially inert with respect to the compound and include waxes, oils, or solids such as carbon black or silica.

In a separate embodiment, the triazinanes of the present invention have a separate primary utility or functionality (such as a coating, lubricant, oil, fuel additive or fuel composition) and include a functional ingredient and the triazinanes of the present invention as a component. The functional ingredient is typically a degradable material such as a hydrocarbon but may also include other degradable materials. This embodiment therefore encompasses for example, a lubricant composition that includes a lubricant as the functional ingredient and the compound of the present invention. This embodiment further encompasses a combustible fuel composition that includes a combustible fuel as the functional ingredient and the compound of the present invention. This embodiment further encompasses a fuel additive composition that includes a fuel additive as the functional ingredient and the compound of the present invention.

In a further embodiment, the triazinanes of the present invention have a separate primary utility or functionality as a pre-cursor material to develop an intermediate that will impart sulfur functionalities on polymeric fiber materials such as para-aramid short fibers, polyethylene terephthalate fibers, and or sulfo-polyester fibers. The functionality will improve vulcanized rubber adhesion to the aforementioned fiber materials for use in a variety of applications. Potentially these composites could be used as a reinforcing additive where the sulfur functionality is critical. Potential routes to create such intermediates include pre-reacting an accelerator such as a sulfenamide with the triazinanes of the present invention and free rubber maker sulfur to create a sulfonated intermediate.

A person skilled in the art will recognize that the measurements described herein are standard measurements that can be obtained by a variety of different test methods. The test methods described represents only one available method to obtain each of the required measurements.

The foregoing description of various embodiments of the invention has been presented for purposes of illustration and description. It is not intended to be exhaustive or to limit the invention to the precise embodiments disclosed. Numerous modifications or variations are possible, in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

Precursors for compounds of the present invention, the compounds of the present invention and methods for their manufacture are illustrated by the following examples, which are not intended in to any limit the spirit or scope of the present invention.

Example 1: Preparation of Sodium S,S',S"-((1,3,5-triazinane-1,3,5-triyl)tris(propane-3,1-diyl)) tris(sulfurothioate)

To a 250 mL round bottom flask fitted with a stir-bar and a reflux condenser were charged 3-chloropropylamine hydrochloride (22.0 g; 169.2 mmol), DI water (84 mL), and sodium thiosulfate pentahydrate (43.6 g; 175.7 mmol of thiosulfate). The reaction mixture was stirred under N2 protection and heated to 100° C. (oil bath temperature) for 1.5 hours. The mixture was allowed to cool to room temperature, then chilled with a cold tap water bath. NaOH (7.0 g; 175.0 mmol) was loaded at once and the reaction mixture was stirred for 0.5 hour to complete deprotonation of the ammonium. Aqueous 37% formaldehyde (14.0 mL; 188.0 mmol of formaldehyde) was dropwise added (syringe) over 4 min (a slight exothermic reaction ensued). A white solid formed readily during the addition of formaldehyde solution. The chilling bath was removed. The reaction mixture was stirred at room temperature for 4 hours. The formed solid was collected by vacuum filtration (Buchner—filter paper), rinsed quickly with DI water (40 mL), and dried at 40-42° C. under vacuum for 20-22 hours. The thin white powder weighed 34.0 g (98% of the theoretical) and contained about 9.3 wt % water according to proton NMR at 60 MHz in anhydrous DMSO-d6.

The first chemical transformation thus entails the reaction of 3-chloropropylammonium chloride with sodium thiosulfate in hot water. The nucleophilic sulfide anion (in sodium thiosulfate) cleanly attacks the electrophilic methylene alpha to the chlorine atom (in 3-chloropropylammonium chloride) to form the S-alkyl sodium thiosulfate function. One equivalent of sodium chloride is by-produced during this step. This transformation can conveniently be monitored by proton NMR at 60 MHz. The disappearance of the peak at 4.0 ppm (two methylenic protons alpha to chlorine atom) is complete after 1.5 hour of reaction at 90-100 deg C. Also, carbon 13 NMR at 15 MHz confirms the targeted transformation took place.

Next, the ammonium is deprotonated by sodium hydroxide at room temperature to free the amine (one more equivalent of sodium chloride is produced here). Low field proton and carbon 13 NMR may be used again to confirm the success of the second step.

Finally, aqueous formaldehyde is slowly added to condense with the primary amine. This transformation leads to the connection of three alkyl sodium thiosulfates by formation of the triazinane core. The desired compound, which precipitates out as a white powder, is simply collected by filtration, washed with water, and dried at 40° C. under vacuum.

Figure 2:
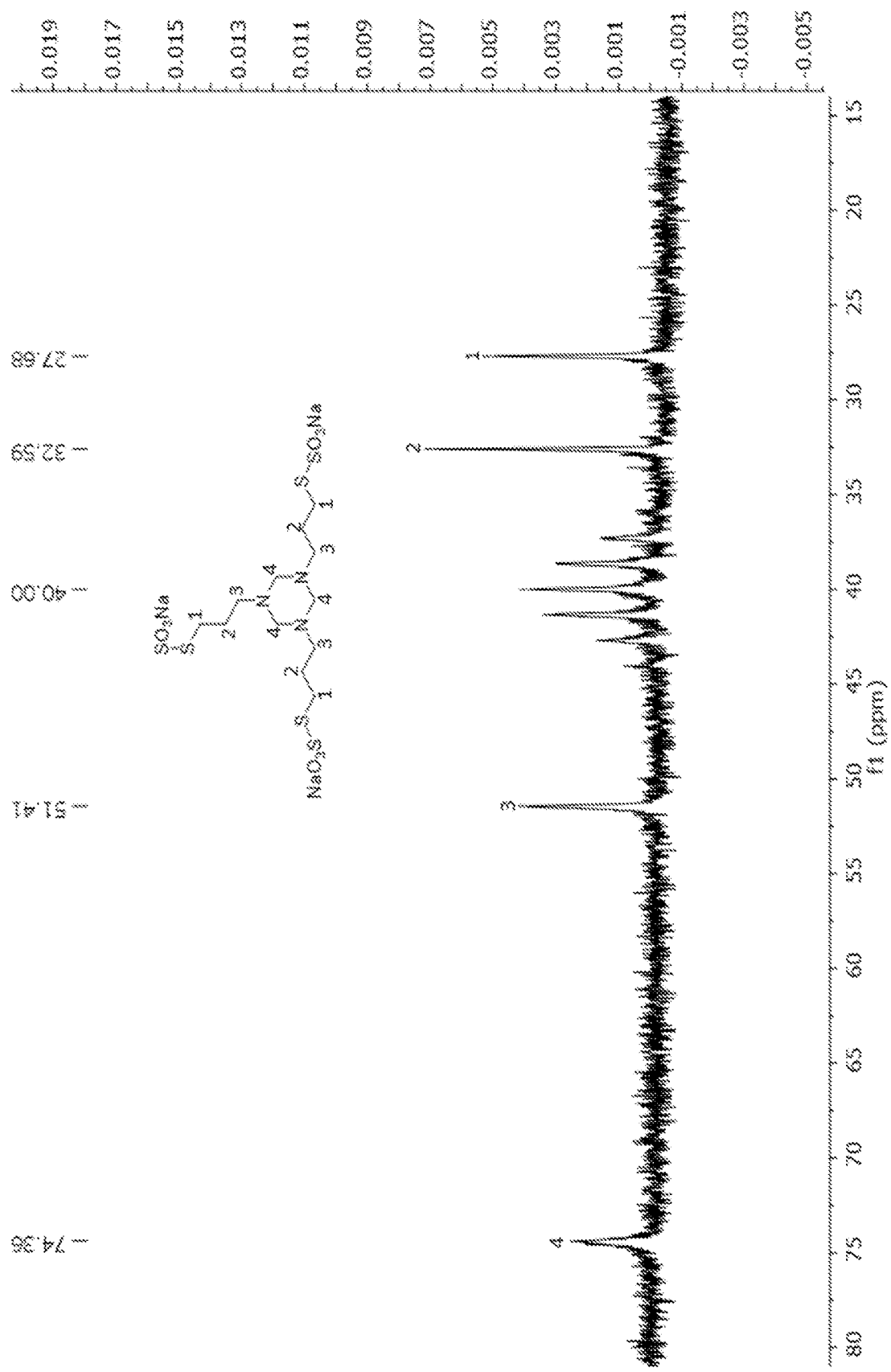

The final material is a superb white powder containing about 3.5 mol water of hydration per mol titled compound as measured by proton NMR at 60 MHz, as depicted in FIG. 1. Carbon 13 NMR at 15 MHz analysis of the final material displays the expected four peaks, as seen in FIG. 2. TGA under N2 protection of the final material shows good stability up to about 160° C.

Example 2: Use of Sodium S,S',S"-((1,3,5-triazinane-1,3,5-triyl)tris(propane-3,1-diyl)) tris(sulfurothioate) in Steel Skim Formulations In this example, rubber formulations were prepared using the triazinane of Example 1 as coat (skim) formulations on brass coated steel components. As can be seen in Table 1, these formulations are natural poly-isoprene with a carbon black of the N300 series, a bond adhesion promoter in the form of cobalt fatty acid salts. A model coat (skim) formulation with cobalt fatty acid salts can be seen as Control 1 in Table 1. Control 2 is a steel skim formulation with a well-known bis-thiosulfate salt, Duralink HIS available from Eastman Chemical Company. Formulations with the triazinane of Example 1 can be seen in Examples 2A and 2B.

TABLE 1

| Material | Control 1 | Control 2 | Example 2A | Example 2B |
|---|---|---|---|---|
| Natural Polyisoprene | 100 | 100 | 100 | 100 |
| N326 | 68 | 68 | 68 | 68 |
| Stearic Acid | 2 | 2 | 2 | 2 |
| Calsol 8240 | 3 | 3 | 3 | 3 |
| Impera 1507 | 3 | 3 | 3 | 3 |
| Cobalt Neodecanoate (20.5% Co) | 1 | 0 | 0 | 0 |
| Duralink HTS | 0 | 1 | 0 | 0 |
| Zinc Oxide | 8 | 8 | 8 | 8 |
| TMQ | 0.7 | 0.7 | 0.7 | 0.7 |
| Triazinane | | | 1 | 3 |
| 6 PPD | 2 | 2 | 2 | 2 |
| Crystex HD OT 20 | 5 | 5 | 5 | 5 |
| DCBS | 1.2 | 1.2 | 1.2 | 1.2 |

It can be seen from the results in Table 2 that the triazinane of the invention gives superior modulus development as shown by Shear Modulus at 10, and 50% strains measured on Rubber Process Analyzer at comparable elongations. The triazinane also shows improvement in reversion resistance as defined by the maximum torque minus the final torque divided by the maximum torque measured in a moving die rheometer. All results are normalized to control 1 & 2 and are summarized in Table 2.

TABLE 2

| Test Parameter | Controls | Example 2A Normalized to Control 1 | Example 2B Normalized to Control 1 | Example 2A Normalized to Control 2 | Example 2B Normalized to Control 2 |
|---|---|---|---|---|---|
| G'10% @ 100 C. 10 Hz | 100 | 113 | 125 | 111 | 124 |
| G'50% @ 100 C. 10 Hz | 100 | 119 | 135 | 109 | 123 |
| Reversion Resistance | 100 | 150 | 161 | 109 | 115 |
| Elongation At Break | 100 | 92 | 90 | 97 | 96 |
| Tb × Eb | 100 | 110 | 113 | 108 | 119 |

In addition, referring to the results in Table 3, steel cord adhesion in both original, aerobic aging (7 & 14 days), and corrosive environments (i.e., Steam at 8, 48 hrs, 5% NaCl at 90 C) show equivalent or superior results.

TABLE 3

| Test Parameter | Controls | Example 2A Normalized to Control 1 | Example 2B Normalized to Control 1 | Example 2A Normalized to Control 2 | Example 2B Normalized to Control 2 |
|---|---|---|---|---|---|
| Steel Cord Adhesion (Unaged) | 100 | 100 | 130 | 110 | 135 |
| Steel Cord Adhesion Aged 7 days 70 C. | 100 | 110 | 140 | 112 | 142 |
| Steel Cord Adhesion Aged 14 days 70 C. | 100 | 95 | 115 | 108 | 112 |
| Steel Cord Adhesion 48 hr steam | 100 | 108 | 109 | 116 | 113 |
| Steel Cord 48 hr 5% NaCl 90 C. | 100 | 109 | 112 | 114 | 116 |
| 6 week 90 C. 95% RH | 100 | 115 | 118 | 121 | 122 |

Example 3: Use of Sodium S,S',S''-((1,3,5-triazinane-1,3,5-triyl)tris(propane-3,1-diyl)) tris(sulfurothioate) in Diene Rubber Formulations In this example, the triazinane of Example 1 is used in combination with two diene rubbers typically used in passenger tire tread caps. The formulation is a blend of two synthetic diene-based polymers and is reinforced with an N200 series carbon black. A typical tread formulation can be seen in Table 4 as Control 1. The formulation containing three parts of the triazinane is indicated as Example 3. This formulation gave superior performance to that of the control.

TABLE 4

| Material | Control 1 | Example 3 |
|---|---|---|
| High Cis Butadiene Rubber (140 Nd) | 25 | 25 |
| SSBR (Firestone Duradene 738) | 75 | 75 |
| Stearic Acid | 5.0 | 5 |
| TDAE Oil (Tudalen 4192) | 26 | 26 |
| Impera 1504 | 15 | 15 |
| Zinc Oxide | 2.5 | 2.5 |
| Triazinane | 0 | 3 |
| 6 PPD | 5 | 5 |
| N234 Carbon Black | 80 | 80 |
| CBTS | 2 | 2 |
| Rubber Maker Sulfur | 1.2 | 1.2 |

The use of triazinane gives improved modulus over a wide range of cure and over-cure conditions, as shown by RPA shear modulus both at 10 and 50% strain in Table 5. In addition, the triazinane gives superior abrasion resistance as determined by Pico abrasion technique. A summary of the normalized properties can be seen in Table 5. In all cases higher values mean more desirable performance properties.

TABLE 5

| Test Parameter | Controls | Example A |
|---|---|---|
| G' @ 10% Cured @ 140 C. | 100 | 108 |
| G' @ 50% Cured at 140 C. | 100 | 108 |
| G' @ 10% Cured at 150 C. | 100 | 105 |
| G' @ 50% Cured at 150 C. | 100 | 104 |
| G' @ 10% Cured at 170 C. | 100 | 110 |
| G' @ 50% Cured at 170 C. | 100 | 109 |
| Abrasion Rate | 100 | 107 |

* All dynamic viscoelastic shear properties tested at 60 C.

Example 4: Use of sodium S,S',S''-((1,3,5-triazinane-1,3,5-triyl)tris(propane-3,1-diyl)) tris(sulfurothioate) in Tread Cap Formulations In this example, the triazinane of Example 1 is used in combination with a diene rubber formulation typically used in passenger tire tread caps. These formulations are characterized by a blend of two synthetic diene based polymers, but are distinguished from Example 2 in that these formulations are reinforced with precipitated silica with the bi-functional silane bis(triethoxysilylpropyl)disulfide rather than carbon black. A typical tread formulation can be seen in Table 6 as Control 1. A formulation containing three parts of triazinane is indicated as Example 4A. As can be seen from Table 7, this formulation gave superior performance to that of the control. In addition, it was noted that the triazinane seems to have strong interactions with silica. As such, a partial substitution of the bis(triethoexysilylpropyl)disulfide was tried, indicated as Example 4B. The viscoelastic properties of both Example(s) 4A & 4B did indeed show superior rubber reinforcing, abrasion resistance, and rubber hysteresis properties over Control 1. In addition, the partial substitution of silane with triazinane showed that you can get the same or similar reinforcing values as determined by G'50%/G'1%. A summary of the physical performance properties can be seen in Table 7 at three typical cure conditions.

TABLE 6

| Material | Control 1 | Example 4A | Example 4B |
|---|---|---|---|
| High Cis Butadiene Rubber (140 Nd) | 25 | 25 | 25 |
| SSBR (Firestone Duradene 738) | 75 | 75 | 75 |
| Stearic Acid | 5.0 | 5 | 5 |
| TDAE Oil (Tudalen 4192) | 26 | 26 | 26 |
| Impera 1504 | 15 | 15 | 15 |
| Zinc Oxide | 2.5 | 2.5 | 2.5 |
| Triazinane | 0 | 3 | 3 |
| 6 PPD | 5 | 5 | 5 |
| Silica | 140 | 140 | 140 |
| TESPD | 8.8 | 8.8 | 4.4 |
| DPG | 3.7 | 3.7 | 3.7 |
| CBTS | 2 | 2 | 2 |
| Rubber Maker Sulfur | 1.2 | 1.2 | 1.2 |

* Silica used was from Evonik 7000 GR.

TABLE 7

| Test Parameter | Controls | Example 4A | Example 4B |
|---|---|---|---|
| G' @ 10% Cured @ 140 C. | 100 | 128 | 122 |
| G' @ 50% Cured @ 140 C. | 100 | 105 | 108 |
| G'50%/G'1% Cured @ 140 C. | 100 | 95 | 105 |
| Tan(delta) @ 10% @ 140 C. | 100 | 103 | 106 |
| G' @ 10% Cured @ 150 C. | 100 | 118 | 121 |
| G' @ 50% Cured at 150 C. | 100 | 103 | 102 |
| G'50%/G'1% Cured @ 150 C. | 100 | 111 | 103 |
| Tan(delta) @ 10% @ 150 C. | 100 | 110 | 103 |
| G' @ 10% Cured @ 170 C. | 100 | 109 | 111 |
| G' @ 50% Cured @ 170 C. | 100 | 100 | 103 |
| G'50%/G'1% @ 170 C. | 100 | 98 | 102 |
| Tan(delta) @ 10% @ 170 C. | 100 | 107 | 106 |
| Pico Volume Loss | 100 | 131 | 111 |

* All Dynamic Shear Modulus Values are tested at 60 C.

Example 5: Use of sodium S,S',S"-((1,3,5-triazinane-1,3,5-triyl)tris(propane-3,1-diyl)) tris(sulfurothioate) in all-Natural Rubber Cap Formulations In this example, the triazinane of Example 1 was used in combination with a diene rubber used typically in heavy (commercial) tire tread caps. The formula was reinforced with a blend of carbon black and precipitate silica. The carbon black used was N110. A typical tread formulation can be seen in Table 8 as Control 1. A formulation containing three parts of triazinane is indicated as Example 5A. As can be seen in Table 9, this formulation gave superior performance to that of the control. Specifically, improved modulus buildup for improved handling and wear, reduced hysteresis at high temperature and 10% strain typically correlated with rolling resistance, improved abrasion resistance, and improved resistance to reversion was observed under a wide range of curing conditions. A summary of the physical performance properties can be seen in Table 9 at two typical cure conditions.

TABLE 8

| Material | Control 1 | Example 5A |
|---|---|---|
| Natural Rubber (SIR - 10) | 100 | 100 |
| N110 Carbon Black | 43 | 43 |
| Stearic Acid | 3 | 3 |
| Wax (Nocheck 472A) | 2 | 2 |
| Zinc Oxide | 3 | 3 |
| Triazine | 0 | 3 |
| 6 PPD | 3 | 3 |
| Silica | 9 | 9 |
| TBBS | 0.8 | 0.8 |
| Rubber Maker Sulfur | 1.2 | 1.2 |

* Silica used was from Evonik 7000 GR.

TABLE 9

| Test Parameter | Controls | Example A |
|---|---|---|
| G' @ 10% Cured @ 140 C. | 100 | 118 |
| G' @ 50% Cured @ 140 C. | 100 | 124 |
| Tan(delta) @ 10% @ 140 C. | 100 | 117 |
| G' @ 10% Cured @ 150 C. | 100 | 103 |
| G' @ 50% Cured at 150 C. | 100 | 103 |
| Tan(delta) @ 10% @ 150 C. | 100 | 100 |
| Picco Volume Loss | 100 | 101 |
| Reversion Resistance @ 170 C. | 100 | 200 |

* All Dynamic Shear Modulus Values are tested at 100 C.

The invention claimed is:

1. A compound represented by formula I:

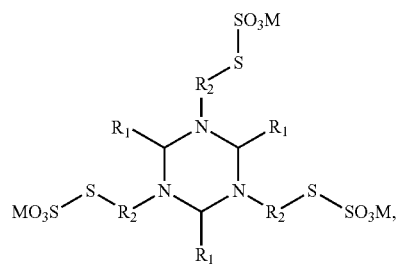

wherein $R_1$ is a hydrogen atom or an alkyl group having from 1 to 2 carbon atoms;
wherein $R_2$ is an alkylene group having from 1 to 12 carbon atoms, an arylene group having from 5 to 18 carbon atoms, or a heterocyclic group having from 5 to 12 carbon atoms; and
wherein M is a monovalent metallic cation; a multivalent metallic cation; or an ammonium or alkyl ammonium cation derived by addition of one or more protons to a nitrogenous base.

2. The compound of claim 1, wherein $R_1$ is a hydrogen atom;
wherein $R_2$ is an alkylene group having from 1 to 5 carbon atoms; and
wherein M is a monovalent metallic cation.

3. The compound of claim 1, wherein $R_1$ is hydrogen;
wherein $R_2$ is an alkylene group having from 1 to 3 carbon atoms; and
wherein M is a monovalent metallic cation or an ammonium or alkyl ammonium cation derived by addition of one or more protons to a nitrogenous base.

4. Sodium S,S',S"- ((1,3,5-triazinane-1,3,5-triyl)tris(ethane-2,1-diyl)) tris(sulfurothioate).

5. Sodium S,S',S"- ((1,3,5-triazinane-1,3,5-triyl)tris(propane-3,1-diyl)) tris(sulfurothioate).

6. Sodium S,S',S"- ((1,3,5-triazinane-1,3,5-triyl)tris(butane-4,1-diyl)) tris(sulfurothioate).

7. Sodium S,S',S"- ((1,3,5-triazinane-1,3,5-triyl)tris(pentane-5,1-diyl)) tris(sulfurothioate).

8. A method of making the compound of claim 1, comprising:
   reacting a haloalkylamine hydrohalide with a metal thiosulfate to obtain an alkylammonium halide thiosulfate metal salt;
   deprotonating the alkylammonium halide thiosulfate metal salt to obtain an alkylammonium thiosulfate metal salt; and
   reacting the alkylammonium thiosulfate metal salt with an aldehyde to obtain the compound of claim 1.

9. The method of claim 8, wherein the haloalkylamine hydrohalide comprises 3-chloropropyl amine hydrochloride, the metal thiosulfate comprises sodium thiosulfate, and the aldehyde comprises formaldehyde.

10. An adhesion-promoting composition comprising the compound of claim 1 and optionally a carrier for said compound.

11. A stabilizer composition comprising the compound of claim 1 and optionally a carrier for said compound.

12. A vulcanizable elastomeric formulation comprising an elastomer and the compound of claim 1.

13. The formulation of claim 12 wherein the compound is present in an amount of from 0.01 to 30 parts per 100 parts of elastomer by weight.

14. The formulation of claim 12 wherein the compound is present in an amount of from 0.1 to 5.0 parts per 100 parts of elastomer by weight.

15. A vulcanized elastomeric article formed from the vulcanizable elastomeric formulation of claim 12.

16. The vulcanized elastomeric article of claim 15 wherein said vulcanized elastomeric article is a vehicle tire.

17. The vulcanized elastomeric article of claim 15, wherein said vulcanized elastomeric article is a sidewall.

18. A combustible fuel composition comprising a combustible fuel and the compound of claim 1.

19. A fuel additive composition comprising a fuel additive and the compound of claim 1.

20. A wire-reinforced rubber component formed from the vulcanizable elastomeric formulation of claim 12.

* * * * *